United States Patent [19]

Ohshima et al.

[11] Patent Number: 4,508,450
[45] Date of Patent: Apr. 2, 1985

[54] SYSTEM FOR CHECKING DEFECTS ON A FLAT SURFACE OF AN OBJECT

[75] Inventors: Ken Ohshima; Masaharu Sakamoto, both of Tokyo, Japan

[73] Assignee: Olympus Optical Co., Ltd., Tokyo, Japan

[21] Appl. No.: 362,621

[22] Filed: Mar. 29, 1982

[30] Foreign Application Priority Data

Mar. 31, 1981 [JP] Japan ............................... 56-48004

[51] Int. Cl.$^3$ ............................................. G01N 21/88
[52] U.S. Cl. ..................................... 356/237; 250/563
[58] Field of Search ............... 356/431, 237; 250/563

[56] References Cited

U.S. PATENT DOCUMENTS

| | | | |
|---|---|---|---|
| 3,898,469 | 8/1975 | Nichols et al. | 250/563 |
| 4,110,048 | 8/1978 | Akutsu et al. | 356/431 |
| 4,223,346 | 9/1980 | Neiheisel et al. | 356/237 X |
| 4,314,763 | 2/1982 | Steigmeier et al. | 356/237 |
| 4,412,743 | 11/1983 | Eberly | 356/237 |

*Primary Examiner*—Vincent P. McGraw
*Attorney, Agent, or Firm*—Frishauf, Holtz, Goodman and Woodward

[57] ABSTRACT

A checking system for checking defects on an optically flat surface of an object to be checked is adapted to spirally scan the surface of the object with a laser beam which is projected from an optical head. The laser beam is reflected from the surface of the object and converted by a photodetector to an electric signal. The level of the electric signal is compared with a reference level to produce a defect signal. The rotation of the object is detected by a position sensor. A counter counts a position signal in response to the defect signal and the contents of the counter is stored, as data representing a defect start position, in a defect position memory. The length data of the defect signal is counted and stored in a defect length memory. Predetermined defect position data is read out of a defect position memory, while defect length data corresponding to the defect position data is read out of the defect length memory. Position data associated with an area to be displayed is compared with defect position data. When both data coincide with each other, the corresponding defect length data is counted down. During the down count period, defect picture element data is stored in a refresh memory. The picture element data stored in the refresh memory is delivered to a CRT where it is displayed as defect data.

5 Claims, 33 Drawing Figures

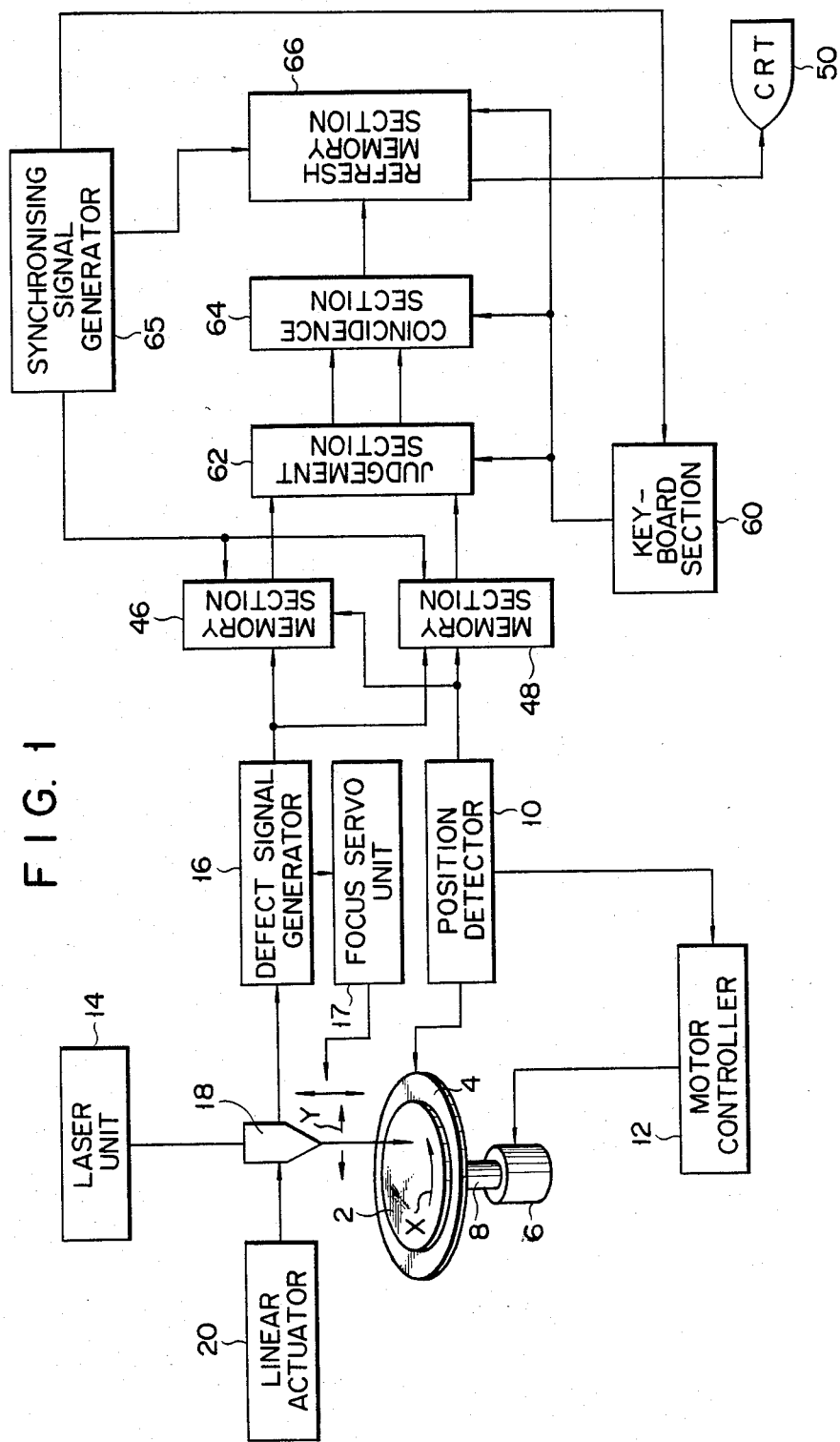
F I G. 1

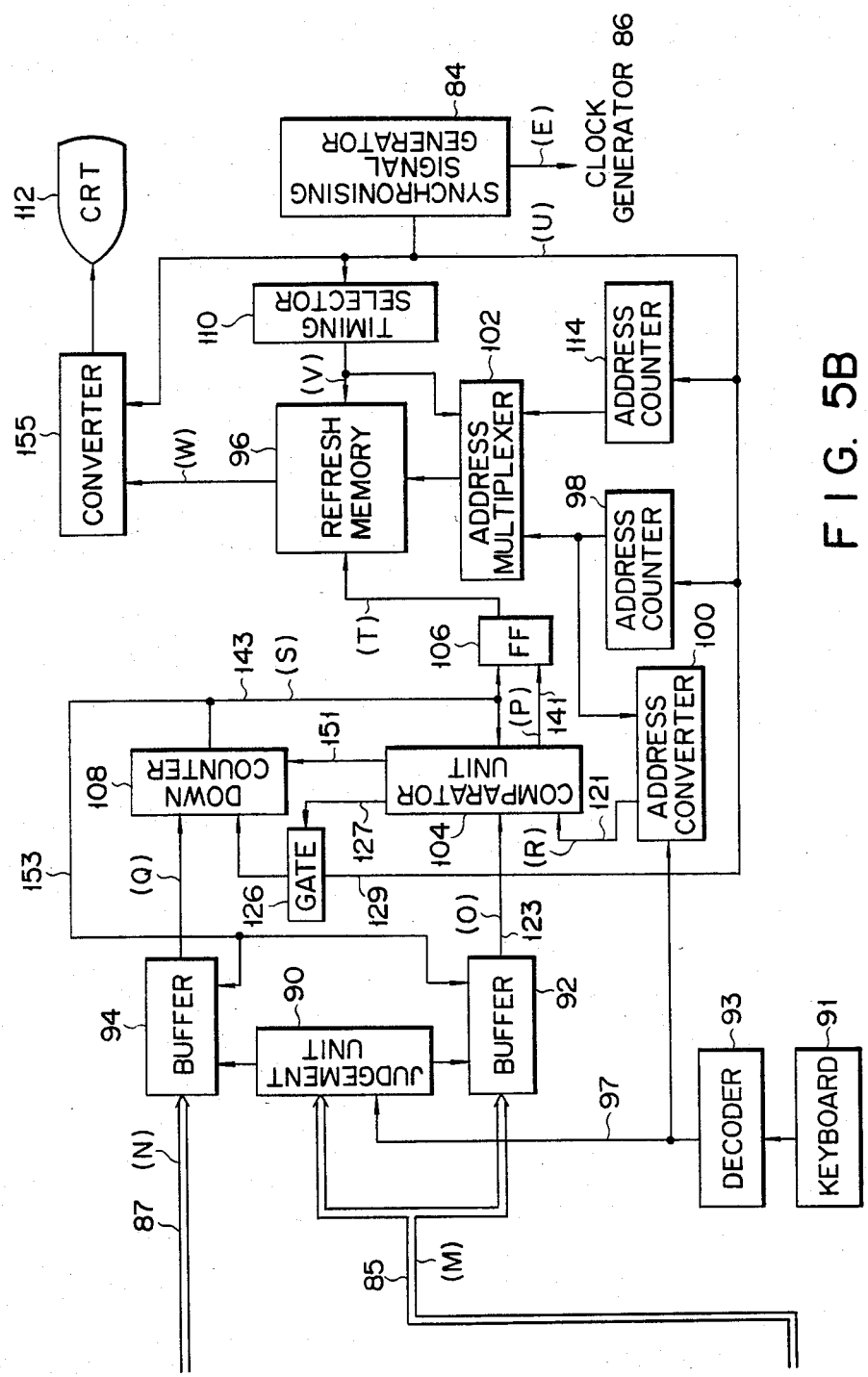
F I G. 5B

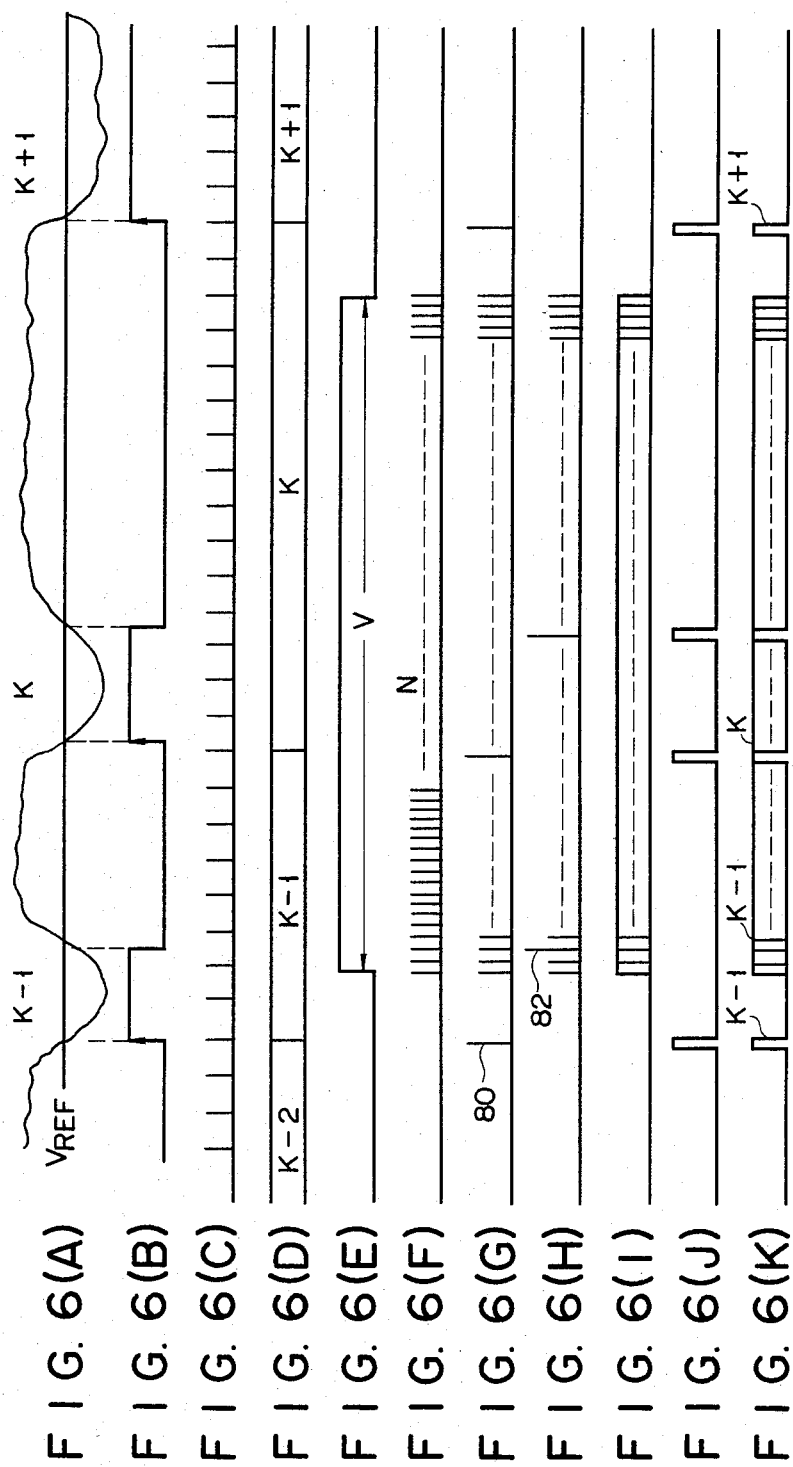

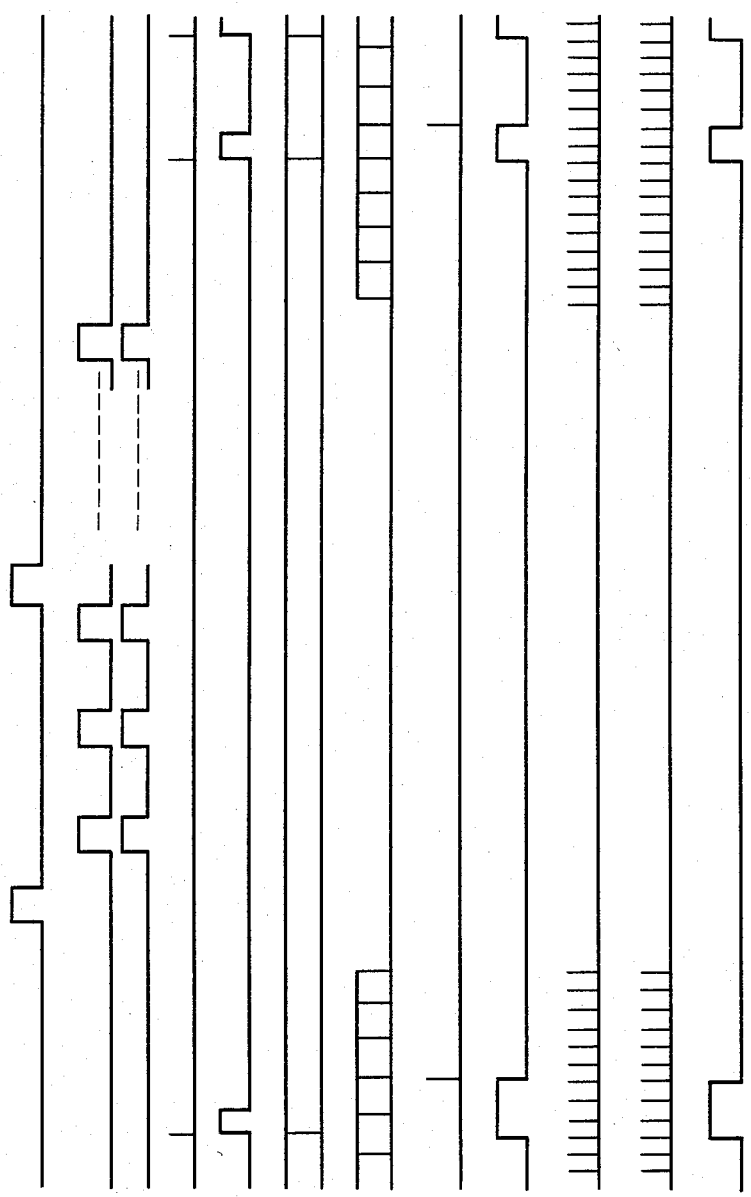

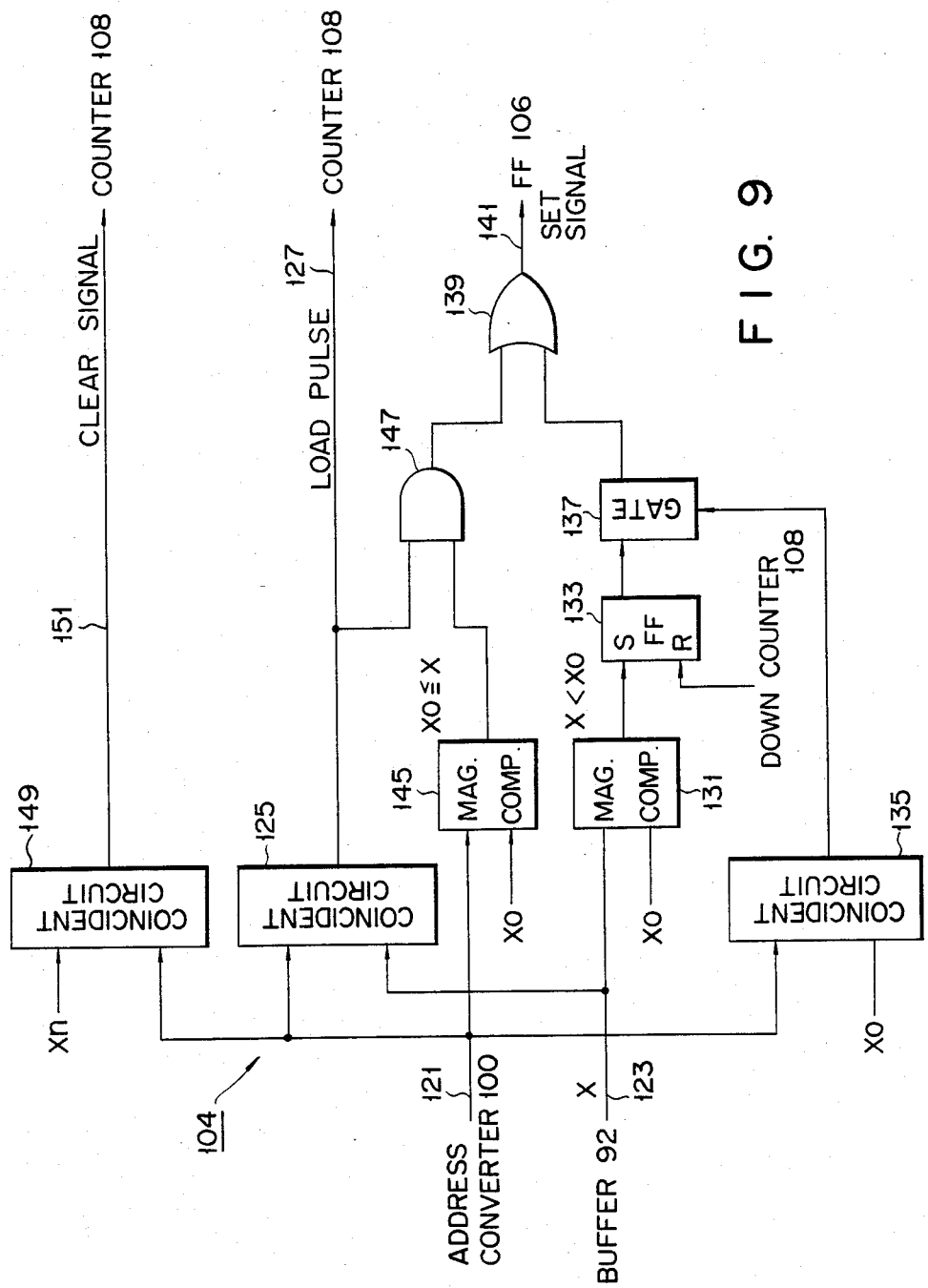
F I G. 9

SYSTEM FOR CHECKING DEFECTS ON A FLAT SURFACE OF AN OBJECT

BACKGROUND OF THE INVENTION

The invention relates to system for checking defects on the surface of an object such as an original glass plate or a wafer.

An eye-viewing method is conventionally adopted to find out defects on the surface of an object such as a wafer. That is, the method comprises magnifying the surface area to be checked under a microscope to permit observation, or causing an image obtained through the microscope to be displayed on the screen of a CRT. Such method depends largely upon the experience of a checker and lacks a certainty and reliability. Moreover, problems also arise such as limited checking speeds, failure to effect rapid checking, etc.

SUMMARY OF THE INVENTION

An object of this invention is to provide a checking system for rapidly and positively checking defects developed on the surface of an object.

Another object of this invention is to provide a checking system for checking defects developed on the surface of an object, in which defect data is stored in a memory of a relatively small capacity.

According to this invention there is provided a checking system for checking defects on a flat surface of an object, comprising:
means for generating laser beams;
means for projecting the laser beams onto the surface of the object and for directing the laser beam reflected from the surface of said object in a given direction;
means for scanning the surface of the object with the laser beam;
means for detecting the reflected laser beam from the projecting means and converting it to an electric signal;
means for comparing the level of an electrical signal from the detecting means with a reference level to produce a defect signal corresponding to a defect on the surface of the object;
means for sequentially generating a position signal associated with a position on the object scanned with the laser beam;
first means for storing the position signal as defect start position data in response to the defect signal; and
second means for storing data corresponding to the length of the defect signal as defect length data.

BRIEF DESCRIPTION OF THE DRAWINGS

FIG. 1 is a block diagram showing a checking system according to one embodiment of this invention;

FIGS. 5A and 5B show a block diagram showing a detail of a system of FIG. 1;

FIGS. 6(A) to 6(W) show a timing chart of signals associated with respective parts of FIGS. 5A and 5B with characters (A) to (W) attached to the lines of FIGS. 5A to 5B;

FIG. 9 is a block diagram showing a detail of a comparator unit as shown in FIG. 5B.

DETAILED DESCRIPTION OF THE PREFERRED EMBODIMENT

Figure 2:
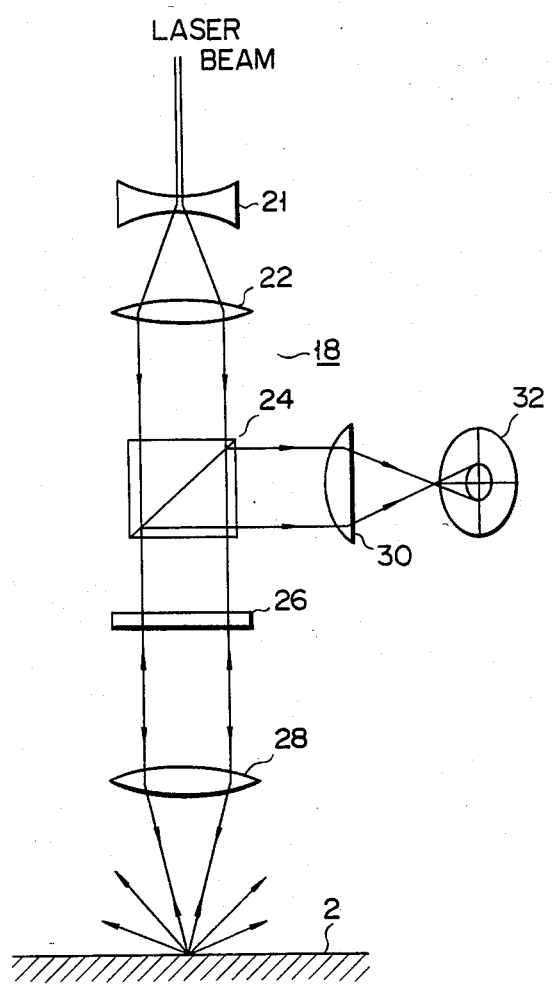
FIG. 2 shows an optical arrangement having an optical head as shown in FIG. 1.

FIG. 1 is a block diagram showing a checking system according to one embodiment of this invention. In FIG. 1 a disk 2 having an optically flat surface to be checked, such as an original glass plate or a semiconductor wafer, is supportingly placed on a turntable 4. The turntable 4 is rotatably supported on a rotation shaft 8 of a rotation motor 6. A rotation position detection pattern for permitting detection of the circumferential position, such as a black-and-white stripe pattern, is provided on the outer peripheral portion of the turntable 4. A position detector 10 comprising, for example, a light emitting element and photodetector for detecting the pattern is located in proximity to the turntable 4. The rotation speed of the rotation motor 6 is controlled (for example PLL-controlled) based on a position signal from the position detector 10. A motor controller 12 is connected to the position detector 10 to prevent a phenomenon such as rotation jitters. An optical head 18 is mounted above the turntable 4 to permit a laser beam emitted from a laser unit 14 to be projected convergently onto the disk 2 to be checked and to permit the laser beam reflected onto the disk 2 to be guided into a defect signal generator 16. The optical head 18 is mechanically coupled to a linear actuator 20 adapted to be linearly moved at constant speed along the radial direction of the turntable 4.

Figure 3:
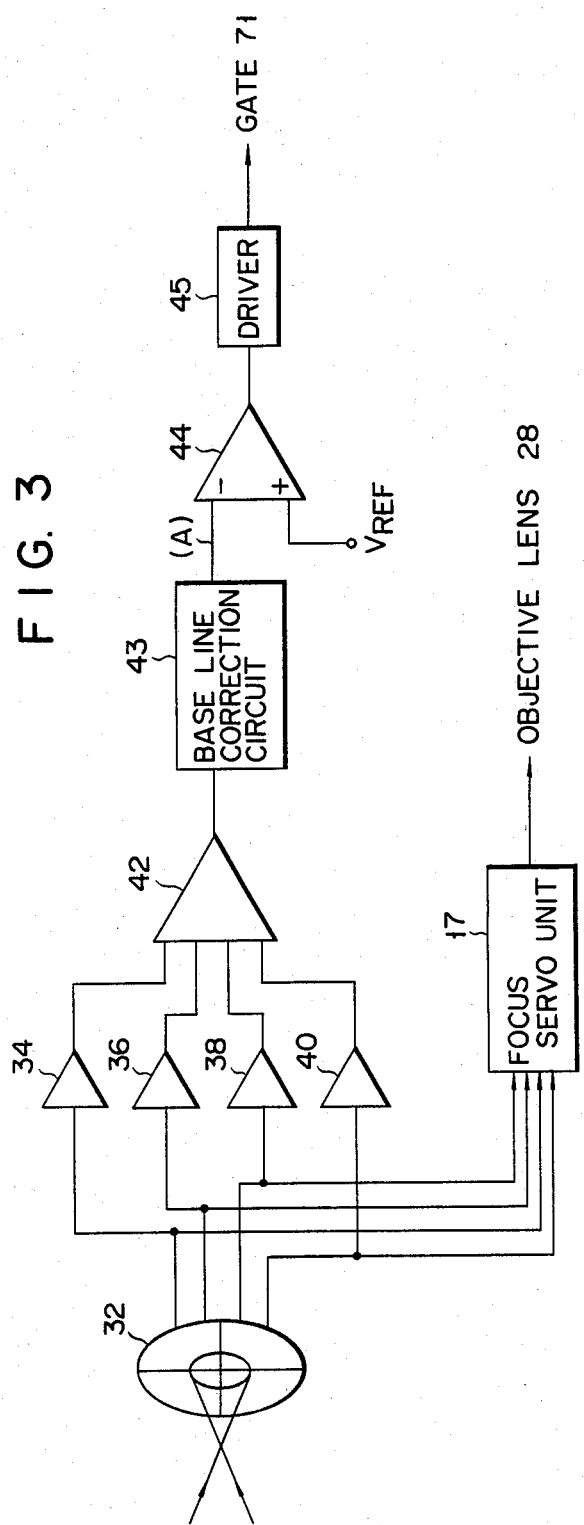
FIG. 3 is a block diagram showing a defect signal generator as shown in FIG. 1.
Figure 4:
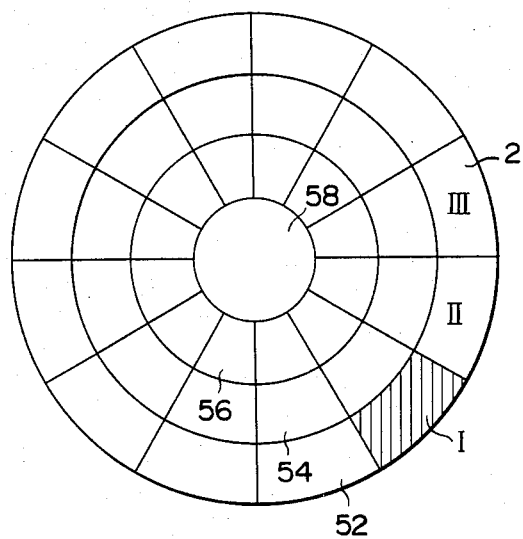
FIG. 4 is a plan view showing a relation of a designated segment area to an area to be checked on an optical disk as shown in FIG. 1.

As shown in FIG. 2, the optical head 18 comprises a concave lens 21 for diverging the laser beam emitted from the laser unit 14, a collimator lens 22 for converting the divergent laser beam to a parallel beam, and a beam splitter 24 for permitting the incident parallel beam to be transmitted and permitting the return parallel beam to be reflected, the polarization plane of the return parallel beam being 90° phase-shifted with respect to the incident beam. A quarter-wave plate 26 and objective lens 28 are arranged on a beam transmitting path of the beam splitter 24, the quarter-wave plate 26 causing the incident beam to be transmitted therethrough to permit the polarization plane to be 45° phase-shifted. The objective lens has its focal point located on the surface of the disk 2. A cylindrical lens 30 and photodetector 32 are arranged on the beam reflecting path of the beam splitter 24. The cylindrical lens 30 has lateral and longitudinal magnifications which are different each other. The photodetector 32 of the defect signal generator 16 has four beam receiving areas segmented in a radial direction. A focus servo unit 17 is connected to the defect signal generator 16 and the focal position of the objective lens (convergent lens) 28 is always located on the surface of the disk 2. That is, as disclosed in U.S. Pat. No. 4,079,247, when the objective lens 28 fails to be focused on the surface of the disk, the configuration of the projecting beam spot as produced on the photodetector 32 varies, varying the levels of detection signals from the four beam receiving areas of the photodetector 32. In this case, the objective lens 28 is moved by the focus servo unit 17 to permit it to be focused on the disk 2. When a "defect" signal is produced, the beam receiving areas of the photodetector are connected, as shown in FIG. 3, to an adder 42 through corresponding preamplifiers 34, 36, 38 and 40 in the defect signal generator. The output of the adder 42 is connected through a base line correction circuit 43 to one input of a comparator 44, a reference voltage $V_{REF}$ being supplied to the other input of the comparator. That is, the objective lens 28 is focused on the defectless area on the disk 2 and, if any beam spot is directed there, nearly all of the beams is regularly reflected. Since in this case the level of the beam added at the adder 42 is greater than that of the reference voltage $V_{REF}$, the output of the comparator 44 is held at a low level. If, on the other hand, the beam spot meets any defect area on the disk 2, the beams are scattered, causing a decrease of the beam components which are regularly reflected there. As a result, the decrease of the beam components is detected at the photodetector 32, causing the level of a beam signal obtained at the adder to become lower than the reference voltage $V_{REF}$ to permit an output of the comparator 44 to be changed to a high level. The disk 2, together with the turntable, is rotated as a unit and the optical head 18 is moved at constant speed, by the linear actuator, in the radial direction of the turntable 4 to permit the disk 2 to be spirally scanned by the beams. Data on the area on the disk 2 is converted to a binary representation which in turn is produced from the comparator 44. That is, where the scanning area is a flat, defectless one, the output of the comparator 44 is held at a low level and, when on the other hand the scanning spot reaches any defect area, the level of the output of the comparator goes high and a "defect" signal of binary representation is produced from the comparator 44. Since the pattern with an adequately small pitch is formed on the outer peripheral portion of the turntable 4 and the pattern is detected by the position detector 10, a position signal representing a given position on the disk 2 which is spirally scanned by the optical head 18 is produced from the position detector 10. The position signal is fed to the motor controller 12, causing the rotation motor 6 to be rotated at constant speed. When a "defect" signal is produced from the comparator 44, it is stored as a circumferential position data and radial position data in a memory section 46 for storing data representing a defect start position. The defect signal generator 16 is connected to the memory section 46 and a memory section for storing data representing the length of the defect signal. The position detector 10 is connected to the memory section 46. The memory section 46 includes a counter for counting a peripheral direction signal and radial direction signal representing a scanning position on the disk 2. The counter has its contents counted up, updating the data corresponding to the scanning position irrespective of whether or not there is any defect on the disk 2. When the "defect" signal is fed from the comparator 44 in the defect signal generator 16 through a driver 45, the count value of the counter is stored in the memory section 46 in response to a rise of the "defect" signal i.e. the position data comprised of the peripheral direction data and radial direction data corresponding to a defect start position is stored in the memory section 46. The memory section 48 includes a counter which is cleared in response to a rise of the "defect" signal and begins to count the "defect" signal and which is stopped in response to a fall of the "defect" signal to permit the count value to be stored in the memory section 48. By so doing, data representing the defect length is stored. The memory sections 46 and 48 are comprised of, for example, an FIFO or a RAM. Where these memory sections are made of RAM, an address generator is provided to permit the position data and defect length data to be written into the memory sections at the same address and to permit these data to be read out of these memory sections 46, 48. Where defects are found on the disk 2 during the spiral scanning, corresponding signals are sequentially produced to permit corresponding defect position data and defect length data to be continuously stored in the memory sections 46 and 48, respectively. When a certain range of a scanning complete area on the disk 2 is reached, the defects on the disk 2 can be displayed on the screen of CRT 50. Where only an outer marginal area 52 of four division areas 52, 54, 56 and 58 of a concentric circle on the surface of the disk 2 is spirally scanned, areas I, II, III, etc. readily segmented on the outer marginal area 52 on the disk 2 is permitted to be displayed on the screen of CRT 50. When an area designating signal corresponding to the segment area I is produced by the actuation of keys on a keyboard section 60, data on the position and length of the defect on the area I and additional area as later described are fed from the memory sections 46 and 48 through a judgment section 62 to a defect start position coincidence circuit section 64. The reason why data on the additional area is read out of the circuit section 64 is as follows. Because the defect position data shows a defect start position, if a position data comparison is performed only within the segment area I, there is a possibility that the defect start position data will not be read out because the defect start position is not present in the segment area I in spite of the fact that the defect is extended into the segment area I. With this in mind a maximum checkable defect length is initially determined and the above-mentioned additional area is determined based on the maximum checkable defect length. By so doing, it is possible to read out such defect even if a defect ending position is reached into the segment region I. A read/write operation is asynchronously performed with respect to the memory sections 46, 48. The read operation is performed in synchronism with a read-out clock which is produced in response to a vertical synchronizing signal from a synchronizing signal generator 65. When the clock from the synchronizing signal generator 65 is supplied to the memory sections 46 and 48, data on the position and length of the defect is read from the memory sections 46 and 48 onto the judgment circuit section 62. The defect position data so read out is compared with area data comprised of a circumferential position data and radial position data associated with the segment area I and additional area, the circumferential position data and radial position data being inputted by the actuation of the keys on the keyboard. When the defect position data is found to be within the area mentioned, it is supplied, together with the defect length data, to the coincidence circuit section 64. In the coincidence circuit section 64, address data representing picture element positions on the display area and addition area of CRT 50 are converted to picture element position data, comprised of the circumferential direction picture element position data and radial direction picture element position data, based on the area designating data which is supplied by the actuation of keys on the keyboard. The picture element position data so converted is compared with a defect position signal sent through the judgment circuit section. When both coincide with each other, a defect representing signal is supplied from the coincidence circuit section to a refresh memory 66. At the same time, the counter stored with the defect signal length data counts down by the clock from the synchronizing signal generator 65. When the contents of the counter becomes zero, a supply of the defect representing signal is stopped. The defect representing signal is written into the refresh memory section 66 at a predetermined address according to the picture element position address. The picture element position data, representing the defect and the defectless position on the disk 2, stored in the fresh memory section is repetitively read out and the segment area I and its contour on the disk 2 are displayed on the screen of CRT 50. When the another segment area is designated and an area designating signal representing another segment area is inputted by the actuation of the key on the keyboard 60, the contents of the refresh memory section is cleared by a clear signal from the keyboard 60. The operation of the checking system of FIG. 1 will be explained below in more detail by referring to FIGS. 5A, 5B, 6(A) to 6(W) and 7 to 9. The same reference numerals are used in these Figures to denote the same parts or elements corresponding to those as shown in the preceding Figures, and further explanation is therefore omitted.

A signal including defect data, as shown in FIG. 6(A), is generated from an adder 42 in the defect signal generator 16, while a disk 2 is spirally scanned by a laser beam projected from an optical head 18. The signal as shown in FIG. 6(A) becomes lower than the reference level $V_{REF}$ when defects $K-1$, $K$ and $K+1$ are present on the disk 2 and is held at a high level when there are no defects on the disk 2. An output signal from the adder 42 is converted to a binary representation by being compared by a comparator 42 with the reference voltage $V_{REF}$. That is, as shown in FIG. 6(B) an output from the comparator 42 is held at a high level when there are defects on the disk 2 and produces a rectangular wave, and held at a low level, when there are no defects on the disk 2. Since the optical head 18 is moved at constant speed relative to a rotating turntable 4, pulses representing positions including the circumferential position on the turntable 4 are generated from the position detector 10, as shown in FIG. 6(C). Note that in this connection the radial position of an optical head 18 is also shown from the circumferential position on the turntable 4. The pulses are supplied to a position counter unit 68, of which the first counter counts them. The first counter clears its contents for each rotation of the turntable 4 and produces pulses representing the radial position. The pulses are supplied to a second counter in the counter unit 68, where they are counted. That is, the first counter generates data X representing the circumferential position of the head 18 relative to the turntable 4 and the second counter generates data Y representing the radial position of the head 18 relative to the turntable 4. When the defect $K-1$ on the disk 2 as shown in FIG. 6(A) is scanned, the contents of a memory address counter 70 is counted up in response to a rise of a "defect" signal of binary representation as shown in FIG. 6(B). The memory address counter 70 generates a write address $(K-1)$ as shown in FIG. 6(D). In response to a write signal (see FIG. 6(J)) from a timing selector 78 a write address $[K-1]$ is supplied, as shown in FIG. 6(K), to a defect signal start position memory 74 and defect signal length memory 76 through an address multiplexer 72. At the rise of the "defect" signal as shown in FIG. 6(B) the contents of a counter 75 is cleared and at the same time a gate 71 is opened.

Thus, clock pulses supplied from a clock generator 73 through the gate 71 are counted at a counter 75 and at the fall of the "defect" signal the gate 71 is closed, stopping a supply of the clock pulses to the counter 75. Therefore, the contents of the counter 75 shows a length of the defect signal. At the rise of the "defect" signal a timing selector 78 supplies a write instruction as indicated by 80 in FIG. 6(G) to a defect position memory 76, permitting position data to be supplied from the position counter unit 68 over a bus line 77 to the defect position memory 76 where it is stored at an address $[K-1]$ thereof. Likewise, at the fall of the "defect" signal the timing selector 78 supplies a write instruction as indicated by 82 in FIG. 6(H) to the defect length memory 74, permitting defect length data as shown in FIG. 6(H) to be supplied from the length counter by way of a bus 79 to the defect length memory where it is stored at an address $[K-1]$ thereof. Likewise, defect position data and defect length data are supplied to the defect position memory 76 and defect length memory 74 where they are stored at addresses $[K]$ and $[K+1]$ thereof.

Now suppose that the disk 2 has, for example, 30 cm in diameter and that scanning is effected over a range 50 to 150 mm from the outer periphery of the disk 2. In order to resolve a 2 μm-long defect on the disk 2, it is necessary to provide signals corresponding to more than 50,000 spots in the radial direction, as well as signals corresponding to more than 471,239 spots in the circumferential direction. Since more than 50,000 spots are smaller than $2^{16}$ and more than 471,239 spots are smaller than $2^{19}$, 35 bits are required as defect start position data and the first and second counters in the position counter unit 68 have to be comprised of, at least, 19 bits and 16 bits, respectively. It is necessary that only 35 bits are stored in the memory at least one address. Now suppose that only N number of defects at maximum is produced on the disk 2. In this case, count is effected up to and including N and addresses corresponding to N at maximum are produced. With a maximum defect length Lmax initially determined, a counter is adopted which can count the maximum defect length Lmax. Note that the above-mentioned additional area is determined based on the maximum defect length.

Figure 7A:
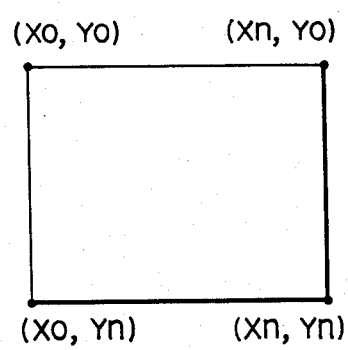
FIG. 7A shows a designated segment area and FIG. 7B shows a segment area including an additional area.
Figure 7B:
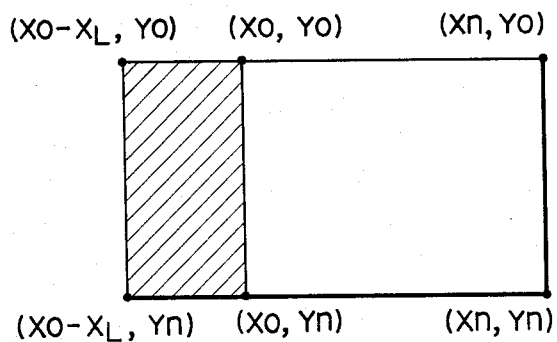
Figure 5A:
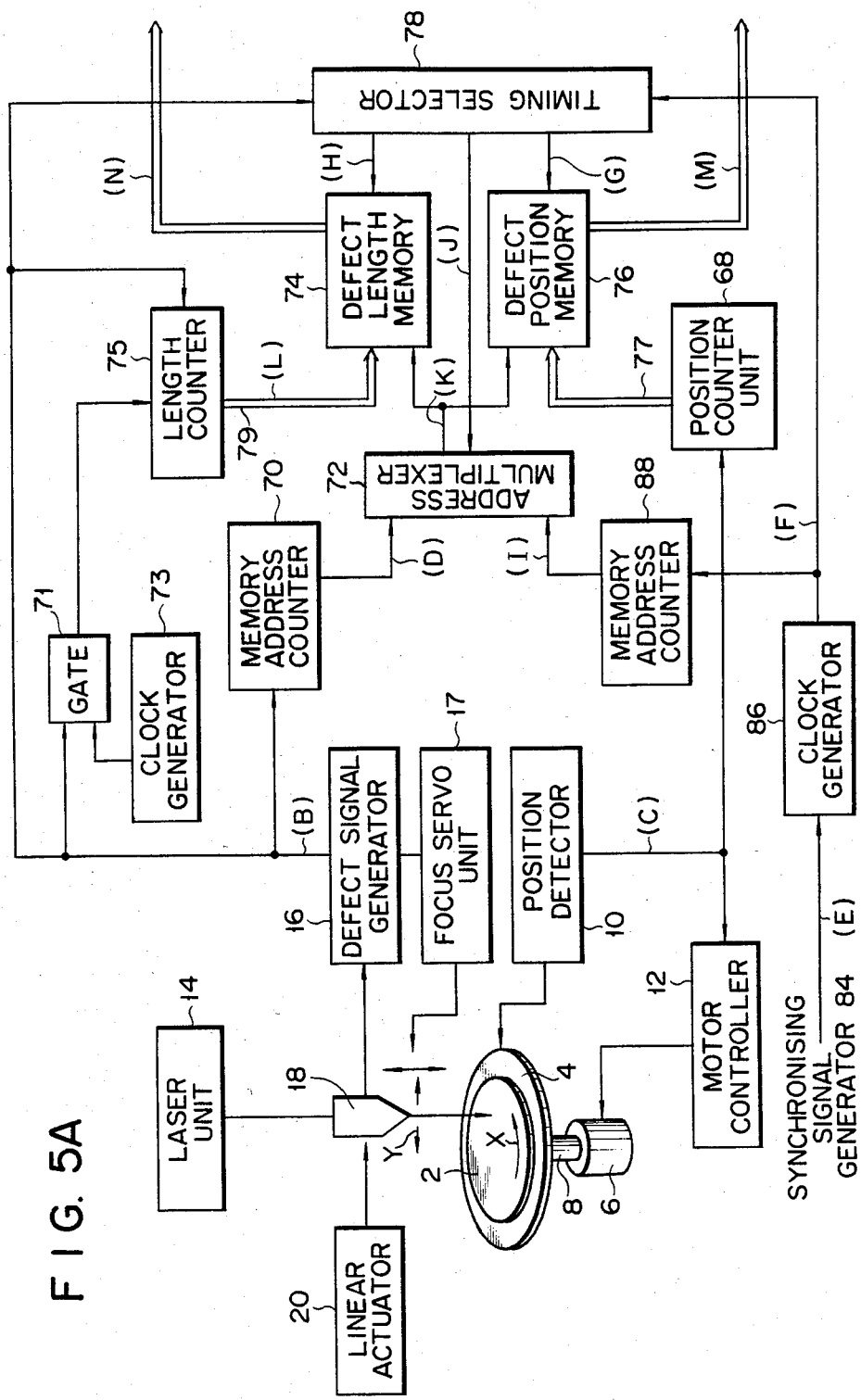
Figure 8:
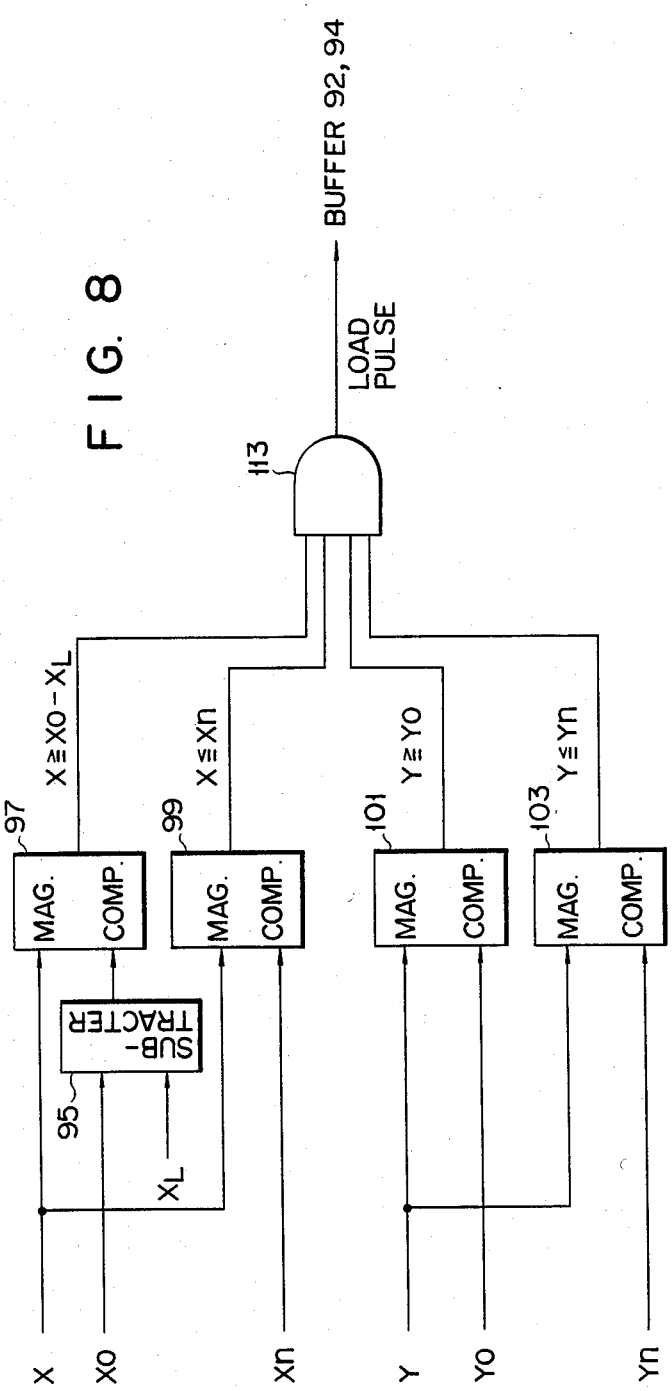
FIG. 8 is a block diagram showing a detail of an area judgement unit of FIG. 5B.

During the vertical blanking period V i.e. the period in which a synchronizing signal as shown in FIG. 6(E) is generated from a synchronizing signal generator as shown in FIG. 5B, defect position data and defect length data are read out of the memories 76 and 74, respectively. When a vertical synchronizing signal becomes a high level, N number of read-out clocks as shown in FIG. 6(F) are supplied, during the vertical blanking period V, from a clock generator 86 to the timing selector 78 and memory address counter 88. The memory address counter 88 sequentially generates an address each time the clock as shown in FIG. 6(I) is inputted. The address as shown in FIG. 6(K) is sequentially supplied through the address multiplexer 72 to the memories 74 and 76. Clocks as shown in FIGS. 6(G) and 6(H) are supplied as read instructions to the memories 74 and 76 through the timing selector 78. The defect position data and defect length data are supplied through data buses 85 and 87 in synchronism with the clocks. The defect position data is supplied through the data bus 85 to an area judgment unit 90. To the unit 90 is supplied through a line 97 area data comprised of circumferential position data and radial position data associated with the segment area to be displayed and additional area. The unit 90 compares the area data with defect position data supplied through the data bus 85 and, when the defect position data is judged as being within a designated segment and additional area, load pulses are supplied to buffers 92 and 94. Defect start position data within the designated segment area as shown in FIG. 6(H) is stored in the buffer 92 and the corresponding defect length data as shown in FIG. 6(N) is stored in buffer 94. Now suppose that as shown in FIG. 7A the segment area selected by the actuation of the key on the keyboard 91 corresponds to the circumferential position data X1 to Xn and radial position data Y1 to Yn. In this case, data corresponding to the designated segment area and the additional area is supplied from a decoder 93 to an area judgment unit. The limit position data X0 from the decoder 93 is supplied to a subtracter 95 to which additional position data $X_L$ for defining the additional area is also inputted. Position data $(X0-X_L)$ is supplied from the subtracter 95 in the unit 90 to a first magnitude comparator 97. Position data X representing a defect start position is inputted from the defect position memory 76 to the magnitude comparator 97, where it is compared with position data $(X0-X_L)$ inputted from the subtracter 95. Where the position data X is greater than the position data $(X0-X_L)$, the output of the first magnitude comparator 97 becomes a logic "1" state. Likewise, the position data X and Xn are supplied to a second magnitude comparator 99 where they are compared with each other. When the position data X is smaller than the limit position Xn, the output of the second magnitude comparator becomes a logic "1" state. When the outputs of the first and second comparators 97 and 99 are both in the logic "1" state, the position data X is in a position range from $(X0-X_L)$ to Xn. The defect position data Y and address position data Y0 are supplied to a magnitude comparator 101 and the defect position data Y and address position data Yn are supplied to a magnitude comparator 103. If the position data Y is greater than the position data Y0 and smaller than Y1, a logic "1" state is obtained from an AND gate 113 connected to the comparators 77, 99, 101 and 103. When the output of the AND gate 113 is at a logic "1" level, it is judged that the position data X and Y are within the area including the designated segment area and the hatched additional area as indicated in FIG. 7B. Since the output of the AND gate 113 is a load signal to be applied to the buffers 94 and 92, only the position data X and Y in the area as shown in FIG. 7B are supplied to the buffer 92 and defect length data corresponding to the position data is supplied to the buffer 94. Here it is to be noted that the value $X_L$ corresponds to the maximum defect length Lmax mentioned. The two buffer memories 92 and 94 have a word depth, i.e. a word stack, greater than a value obtained by dividing the maximum number of defects, N, by the areas segmented on the disk 2. In other words, the maximum number of defects capable of being present in the segment area is initially determined and the buffers 92 and 94 have a word stack of which the capacity is greater than the number of the defects. As evident from the time chart as shown in FIGS. 6(E) to 6(N), the defect data in the segment area is inputted into the buffers 92 and 94 during the vertical blanking period. The data from the buffers 92 and 94 are converted to image data which in turn is delivered to a refresh memory 96 in synchronism with clocks generated from the synchronizing signal generator 84. When write clocks as shown in FIG. 6(U) are generated from the synchronizing signal generator 84, they are supplied to the timing selector 110 and at the same time counted at an address counter 98. The count value of the counter 98 is sequentially supplied as address data to an address converter 100. At the same time, the counted value is supplied to an address multiplexer 102 and then to the refresh memory 96 in synchronism with the synchronizing signal, as shown in FIG. 6(V), from the timing selector. In the address converter 100, the count value of the counter 98 is referred to the designated segment area position data supplied from the decoder 93 and the address data is converted to position data comprised of circumferential position data and radial position data associated with the area including the additional area as shown in FIG. 7B, and supplied to a defect start position comparator unit 104, where the position data is compared with the defect position address data, as shown in FIG. 6(D), from the buffer 92. Where the defect position data of the buffer 92 does not coincide with the position data of the address converter 100, the output of a flip-flop 106 is maintained at a "0" state and the refresh memory 96 continuously stores an output "0" of the flip-flop 106, as a "defectless" picture element, at an address designated by the address counter 98. Where, with the continued address updating, the position data of the address converter 100 coincides with defect position data from the buffer 92, the comparator unit 104 delivers a set signal as shown in FIG. 6(P) to the flip-flop 106 which in turn is maintained at the "1" state as shown in FIG. 6(T). As a result, the defect picture element data is sequentially written into the refresh memory 96 at an address designated by the address counter 98. Defect length data is stored in the buffer memory 94 and a down counter 108 has its contents counted down in synchronism with the clock from the synchronizing signal generator, when a gate 126 is opened by the comparator unit 104. When the contents of the down counter 108 is counted down to zero, it sends a reset signal as shown in FIG. 6(S) through a line 143 to a flip-flop 106 which in turn is reset. In consequence, the output of the flip-flop 106 is changed to zero and the zero output of the flip-flop 106 is stored, as defectless picture element data, in the fresh memory at a corresponding address.

The operation of the comparator unit 104 will be explained in more detail by referring to FIG. 9. As shown in FIG. 9 address position data $X0-X_L$ to Xn are supplied through a line 121 to the comparator 104. Likewise, position data X corresponding to defect start position is supplied to the comparator 104 through a line 123. Now suppose that the defect start position falls within the area $X0-X_L$ to Xn as shown in FIG. 7B and that the defect position data X, corresponding to the defect start position, supplied to a coincidence circuit 125 coincides with the address position data supplied from the address converter 100 to the coincidence circuit 125, the coincidence circuit 125 delivers a load pulse over a line 127 to the gate 126. The gate 126 is opened by a given load pulse, the down counter 108 receives defect length data corresponding to the position data X from the buffer 94, and has its contents continuously counted down upon receipt of the synchronizing pulse. If a defect start position falls within the additional area from $(X0-X_L)$ to X0 as shown in FIG. 7B, since the defect position data X is smaller than data X0 which is initially set, the output of a magnitude comparator 131 becomes a "1" state to permit a flip-flop 133 to be set to a "1" state. When the address position data from the address converter 100 is sequentially updated and data X0 is obtained, a coincidence circuit 135 delivers a "1" state output to a gate 137 which in turn causes is opened to produce a set signal through an OR gate 139. By the set signal the flip-flop circuit 106 is set to produce a "defect" signal. The "defect" signal is sequentially supplied to the refresh memory 96 where it is stored at an address thereof which corresponding to the address produced from the address counter 98. During a time period from the setting of the flip-flop 133 to the opening of the gate 137 the defect length data set at the counter 108 is counted down, but the flip-flop 106 is not set because the gate 137 is closed. When the gate 137 is closed to cause the flip-flop 106 to be set, the defect length data of the down counter 108 is counted down to the defect length as measured from the defect position X0 and the address data is updated to a value corresponding to the defect position X0. As a result, only the defect and defectless data associated with the designated segment area are stored in the fresh memory. When the defect data of the down counter 108 is all counted down, a reset signal is supplied from the down counter 108 through a line 143 to the flip-flop 106, causing it to be reset to a "0" state. The output of the "0" state is supplied from the flip-flop 106 to the refresh memory 96 where it is stored as defectless data at an address thereof corresponding to the address produced from the address counter. If the defect start position falls within a designated segment area X0 to Xn as shown in FIG. 7B, when the defect position data X coincides with the address position data, the coincidence circuit 125 produces a load pulse. When the address position data is greater than the data X0, a magnitude comparator 145 delivers an output signal of a state "1" to an AND gate 147. Since the load pulse is supplied from the coincidence circuit 125 to the AND gate 147, the output of the AND gate 147 is delivered through the OR gate 139 to the flip-flop 106, causing the latter to be set to permit the "defect" data to be stored in the refresh memory 96. When the address position data is updated up to Xn, a clear signal is delivered from a coincidence circuit 149 through a line 151 to the down counter 108 to cause the latter to be cleared. After the address position data and defect start position data reach the position Xn, the load pulse from the coincidence circuit 125 ceases to exist, causing the gate 126 to be closed. After the defect length data set to the down counter 108 is all counted down or the down counter 108 is cleared by a clear signal, a reset signal from the down counter 108 is supplied through a line 153 to the buffers 92 and 94. The defect start position data of the buffers 92 and 94 are updated by the reset signal.

As evident from the above, it follows that the defect length data is stored as defect picture element data in the refresh memory 96. When picture elements enough to be displayed on the screen of a CRT 112 are stored in the refresh memory 96, the timing selector 110 delivers the picture element data as shown in FIG. 6(W) from the refresh memory 96 to the CRT 112 where a defect image associated with the segment area is displayed. The clock from the synchronizing signal generator 84 is supplied to the address counter 114 and timing selector 110. The address counter 114, while counting the clock, produces a picture element position address on the CRT 112. The picture element address from the address counter 114 is supplied through the address multiplexer 102 to the refresh memory 96 by the timing signal as shown in FIG. 6(B). The picture element data is supplied from the refresh memory 96 to a video signal converter 155, in synchronism with the synchronizing signal, where it is converted to a video signal. The video signal is supplied to the CRT 112 where it is displayed.

Although in the above-mentioned embodiment the defect signal is converted to a binary representation showing the presence or absence of the defect, this invention is not restricted thereto. By utilizing the fact that the extent of the defect, such as the depth or the height of the defect, is dependent upon the intensity of the beam, the defect signal may be A/D converted to an image signal of a varying shade corresponding to the extent of the defect according to the level of the signal, and the image signal may be stored in a beam intensity memory. The signal may be displayed on CRT 112 or 50 or be copied on a recording paper on a copying apparatus or be printed on a paper sheet on a printer.

In the embodiment as shown in FIG. 1 the memory section 48 may store a defect ending position. That is, the memory 48 may include a counter, like the memory 46, adapted to count a position signal from the position detector 10 and the count value of the counter may be stored as defect ending position data in the memory 48 according to a fall of the "defect" signal. The defect ending position data may be treated in the same way as the defect length data and used as a defect display.

According to this invention, defects on the disk can be quickly and accurately detected for display on the CRT. A memory for storing defect data may store only defect position data and defect length data without adopting such a system as to permit data storage to be effected in a manner to make the position of an area on the disk correspond to picture elements. The capacity of the memory may be made advantageously smaller. In order to detect defects of 2 μm on the surface of the disk with a diameter of 30 cm and an effective scanning diameter of 10 to 30 cm, a memory capacity of about $6.28 \times 10^{10}$ bits, and hence a bulkier memory, is required. If the number of defects is below 10 K with a defect length of below 1 mm, then a memory capacity is 10 KW−35 bits (the number of bits, $3584 \times 10^5$ bits) for the position data and 10 KW−9 bits (the number of bits, $9216 \times 10^4$ bits) for the defect length data and the total number of bits is $45056 \times 10^5$, a saving of more than $1/10^5$ compared with the above-mentioned system.

What we claim is:

1. A checking system for checking defects on a flat surface of an object to be checked, comprising:
    means for generating laser beams;
    means for projecting the laser beams onto the surface of the object and for directing the laser beam reflected from the surface of said object in a given direction;
    means for scanning the surface of the object with the laser beam;
    means for detecting the laser beam reflected from the projecting means and converting it to an electric signal;
    means for comparing the level of an electric signal from the detecting means with a reference level to produce a defect signal corresponding to a defect on the surface of the object;
    generating means for sequentially generating a position signal associated with a position on the object scanned with the laser beam;

first means for storing the position signal, received from said generating means, as defect start position data in response to the defect signal;

second means for storing data corresponding to the length of the detected defect which in turn corresponds to the length of the defect signal as defect length data;

means for providing said detect start position data on a predetermined portion of the surface area of the object which is less than the whole surface area of the object, and said defect length data associated with said defect start position data corresponding to said predetermined surface area portion;

picture element converting means for converting said defect start position data and said defect length data, provided by said providing means, to picture element data;

third means for storing said picture element data;

read out means for reading said picture element data out of said third means; and means for displaying a defect image of said predetermined surface area portion of the object by using the picture element data read out by said read out means.

2. A checking system according to claim 1, in which said second means includes means for counting the defect signal corresponding to defect length data.

3. A checking system according to claim 1, in which said scanning means comprises means for rotating the object about a shaft disposed normal to a plane of the object; and means for causing said projecting means to be linearly moved above the object in a direction parallel to the plane of said object.

4. A checking system according to claim 3, in which said generating means for generating the position signal comprises means for detecting the rotation of the object and for generating a signal representing a rotation position of the object; and said first means includes means for counting a signal corresponding to the rotation position of the object and means for storing a count value of said counted signal.

5. A checking system according to claim 1, in which said picture element converting means comprises means for producing position data associated with an area to be displayed on said display means; means for comparing the defect start position data with the position data to produce a coincidence signal; means for counting down the defect length data in response to said coincidence signal; and means for producing a defect picture element during a time period in which the defect length data is counted down.

* * * * *